United States Patent [19]
Haffey et al.

[11] Patent Number: 5,120,639
[45] Date of Patent: Jun. 9, 1992

[54] SELECTIVE INHIBITION OF DNA POLYMERASE

[75] Inventors: Mary L. Haffey, Flemington; James T. Matthews, Bedminster, both of N.J.

[73] Assignee: E. R. Squibb & Sons, Inc., Princeton, N.J.

[21] Appl. No.: 332,203

[22] Filed: Apr. 3, 1989

[51] Int. Cl.$^5$ ............................................. C12Q 1/70
[52] U.S. Cl. ........................................ 435/5; 435/7.4; 435/236; 435/184
[58] Field of Search ................ 436/501, 86; 435/69.2, 435/174, 5

[56] References Cited

PUBLICATIONS

Bassiri, R., J. Dvorak, and R. D. Utiger. 1979. pp. 46–47. In B. M. Jaffe and H. R. Behrman (ed.), Methods of hormone radioimmunoassay. Academic Press, Inc., New York.

Becker, Y. 1988. Computer-assisted primary and secondary structure analysis of DNA polymerases of herpes simplex, Epstein-Barr and varicella zoster viruses reveal conserved domains with some homology to DNA-binding domain in E. coil pol I. Virus Genes 1:351–367.

Challberg, M. D. 1986. A method for identifying the viral genes required for herpes virus DNA replication. Proc. Natl. Acad. Sci. USA 83:9094–9099.

Chartrand, P., C. S. Crumpacker, P. A. Schaffer, and N. M. Wilkie. 1980. Physical and genetic analysis of the herpes simple DNA polymerase locus. Virology 103:311–326.

Coen, D. M., D. P. Aschman, P. T. Gelep, M. J. Retondo, S. K. Weller, and P. A. Schaffer. 1984. Fine mapping and molecular cloning of mutations on the herpes simplex virus DNA polymerase locus. J. Virol. 49:236–247.

Dorsky, D. I., Chatis, and C. Crumpacker. 1987. Functional expression of a cloned herpes simplex type 1 DNA polymerase gene. J. Virol. 61:1704–1707.

Furman, P. A., M. H. St. Clair, J. A. Fyfe, J. L. Rideout, P. M. Keller, and G. B. Elion. 1979. Inhibition of herpes simplex virus induced DNA polymerase activity and viral DNA replication by 9-(2-hydroxyethoxymethyl) quanine and its triphosphate: J. Virol. 32:72–77.

Gibbs, J. S., H. C. Chiou, J. D. Hall, D. W. Mount, M. J. Retondo, S. K. Weller, D. M. and Coen. 1985. Sequence and mapping analyses of the herpes simplex virus DNA polymerase gene predict a C-terminal substrate binding domain. Proc. Natl. Acad. Sci. USA 82:7969–7973.

Gibbs, J. S., H. C. Chiou, K. F. Bastow, Y-C. Cheng, and D. M. Coen. 1988. Identification of amino acids in herpes simplex virus DNA polymerase involved in substrate and drug recognition. Proc. Natl. Acad. Sci. USA 85:6672–6676.

Haffey, M. L., J. S. Stevens, B. T. Terry, D. Dorsky, C. S. Crumpacker, S. M. Wietstock, W. T. Ruyechan, and A. K. Field. 1988. Expression of herpes simplex virus type 1 DNA polymerase in *Saccharomyces cerevisiae* and detection of virus-specific enzyme activity in cell-free lysates. J. Virol. 62:4493–4498.

Karkas, J. D., W. T. Ashton, L. F. Canning, R. Liou, J. Germershausen, R. bostedor, B. Arison, A. K. Field and R. L. Tolman. 1986. Enzymatic phosphorylation of the antiherpetic agent 9-[2,3-dihydroxy-1-propoxy)-methyl] guanine. J. Med. Chem. 29:842–848.

Knopf, C. W. 1986. Nucleotide sequence of the DNA polymerase gene of herpes simplex virus type 1 stain Angelotti, nucleic acids Res. 14:8225–8226.

(List continued on next page.)

Primary Examiner—Esther L. Kepplinger
Assistant Examiner—Donna C. Wortman
Attorney, Agent, or Firm—James M. Bogden

[57] ABSTRACT

Two peptides, P6 and P7, having the amino acid sequence APGDEPAPPY and AGATAEETRY have been used to obtain antibodies made against them, which antibodies specifically neutralize HSV-1 and HSV-2 DNA polymerase. The present invention also contemplates a method of screening for inhibitors of HSV-1 and HSV-2 polymerase utilizing the antibodies.

6 Claims, 5 Drawing Sheets

PUBLICATIONS

Knopf, C. W. 1987. The herpes simplex virus type 1 DNA polymerase gene: site of phosphonoacetic acid resistance mutation in strain Angelotti is highly conserved. J. Gen. Virol. 68: 1429–1443.

Kouzarides, T. A. T. Bankier, S. C. Satchwell, K. Weston, P. Tomlinson, and B. G. Barrell. 1987. Sequence and transcription analysis of the human cytomegalovirus DNA polymerase gene. J. Virol. 61:125–133.

Larder, B. A. S. D. Kemp and G. Darby. 1987. Related functional domains in virus DNA polymerases. Embo J. 6:169–175.

Norrby, E., M. A. Mufson, H. Alexander, R. A. Houghten, and R. A. Lerner. 1987. Site-directed serology with synthetic peptides representing the large glycoprotein G of respiratory syncytial virus. Proc. Natl. Acad. Sci. USA 84:6572–6576.

Ostrander, M. and Y. C. Cheng. 1980. Properties of herpes simplex virus type 1 and type 2 DNA polymerases. Biochem. Biophys. Acta 609:232–245.

Ruyechan, W. and A. Weir. 1984. Interaction with nucleic acids and stimulation of the viral DNA polymerase by the herpes simplex virus type 1 major DNA binding protein. J. Virol. 52:727–733.

Thomas, M. S., L. M. Banks, D. J. Purifoy and K. L. Powell. 1988 Production of antibodies of predetermined specificity against herpes simplex virus DNA polymerase and their use in characterization of the enzyme. J. Virol. 62:1550–1557.

Tsurumi, T., K. Maeno and Y. Nishiyama. 1987. Nucleotide sequence of the DNA polymerase of herpes simplex type 2 and comparison with type 1 counterpart. Gene 52:129–137.

Tsurumi, T., K. Maeno and Y. Nishiyama. 1987. A single-base change within the DNA polymerase locus of herpes simplex type 2 can confer resistance to Aphidicolin. J. Virol. 61:2007–2015.

Weisshart, K. and C. W. Knopf. 1988. The herpes simplex virus type 1 DNA Polymerase (Polypeptide structure and antigenic domains). Eur. J. Biochem. 174:707–716.

Wang, T. S., S. W. Wong and D. Korn. 1989. Human DNA polymerase a: predicted functional domains and relationships with viral DNA polymerases. FASEB J. 3:14–21.

Wong, S. W., A. F. Wahl, P. M. Yuan, N. Arai, B. E. Pearson, K-I. Arai, D. Korn, M. W. Hunkapiller and T. S. Wang. 1988. Human DNA polymerase alpha gene expression is cell proliferation dependent and its primary structure is similar to both prokaryotic and eukaryotic replicative DNA polymerases. EMBO J. 7:37–47.

SELECTIVE INHIBITION OF DNA POLYMERASE

FIELD OF THE INVENTION

Synthetic peptides used to generate neutralizing antisera, which antisera inhibit HSV DNA polymerase.

BACKGROUND OF THE INVENTION

The herpes simplex virus (HSV) DNA polymerase (pol) has been shown to be of central importance for viral DNA replication (3,4,5,18) and is one of the major target enzymes of current antiviral chemotherapy. The nucleotide sequences of the HSV-1 and HSV-2 DNA polymerases have been determined in several laboratories (8,12,15,20,23). The sequences suggest that the HSV-1 gene encodes a polypeptide of 1235 amino acids, approximately 136 kDa (8,12,20), and polypeptides of this size have been associated with HSV-specific DNA polymerase activity in infected cells (18,19,22), by in vitro translation (6), and in a yeast expression system (10). The HSV-2 enzyme is 1240 amino acids in length with a molecular weight of 137 kDa and shares 95.5% amino acid sequence homology to the HSV-1 enzyme.

Comparison of the deduced amino acid sequence of the HSV DNA polymerase with other herpesvirus and eukaryotic DNA polymerases (2,8,9, 14,15,26,27) reveals several protein domains which are conserved among the different pol enzymes. The most conserved regions are clustered towards the carboxy terminus. These conserved regions are generally thought to be involved in substrate recognition or catalysis by the DNA pol enzymes (8,9,26,27). In spite of the apparent structural similarities between the mammalian and viral enzymes, the HSV polymerases can readily be distinguished by their enhanced activity in the presence of high salt concentrations and greater sensitivity to such agents as acycloguanosine triphosphate (ACVTP, acyclovir triphosphate) and phosphonoacetate (PAA) (7,17). This suggests that there are some structural differences in the binding sites between these molecules and selective drug development relies, at least in part, upon these subtle differences.

Consistent with comparative sequence analysis, precise mapping of drug resistance and temperature sensitive mutations (4,5,13,14,24) have further suggested that the active site of the enzyme maps within the carboxy terminus of the pol protein, specifically between amino acid residues 597–1008.

In agreement with the functional assignment, Weisshart and Knopf (25) have shown that antibodies raised to the central and the C-terminal portions of the HSV-1 protein inhibited the polymerizing activity by 70-90%, respectively. In contrast, antibodies directed towards the N-terminal HSV-1 domain did not neutralize the enzymatic activity. In addition, amino terminal deletions have been shown to retain HSV-1 DNA pol activity, while carboxy terminal deletions can inactiviate the enzyme (6). Thomas et.al. (22) demonstrated that an antisera to a non-conserved N-terminal peptide (residues 1-15) could immunoprecipitate HSV-1 DNA polymerase activity, but they did not discuss the effect of that antisera on neutralization of enzymatic activity.

The present invention demonstrates that antisera to two distinct carboxy terminal peptides (HSV-1 residues 1100-1108 and 1216-1224) can specifically neutralize HSV-1 and HSV-2 polymerase activity. These peptide sequences are unique to HSV and are not conserved in other herpes viruses or eukaryotic polymerases.

SUMMARY OF THE INVENTION

Two peptides, P6 and P7, having the amino acid sequence APGDEPAPPY and AGATAEETRY have been used to obtain antibodies made against them, which antibodies specifically neutralize HSV-1 and HSV-2 DNA polymerase. The present invention also contemplates a method of screening for inhibitors of HSV-1 and HSV-2 polymerase utilizing the antibodies.

DETAILED DESCRIPTION OF THE INVENTION

Synthetic peptides corresponding to amino acid sequences present in the Herpes Simplex Virus type-1 (HSV-1) (Strain KOS) and HSV-2 (Strain 186) DNA polymerase (pol) polypeptide have been used to generate rabbit polyclonal antisera of defined specificity. The peptides were identified from published HSV pol sequences (8,12,15,20,23) which describe the HSV-1 and HSV-2 pol open reading frame to be 1235 and 1240 amino acids in length, respectively. Peptides were chosen based on several criteria: 1) herpesvirus specificity; 2) strain conservation; and 3) relative hydrophilicity. Three peptides were studied. Two of the peptides, designated P6 and P7, representing amino acid residues 1100-1108 and 1216-1224 of the deduced HSV-1 sequence, produced antisera which could neutralize HSV-1 DNA polymerase activity in a dose-dependent manner. These antisera could also neutralize HSV-2 polymerase, although less efficiently. The endogenous mammalian alpha polymerase activity was completely refractory to the inhibitory effect of these antibodies. In contrast, antiserum to peptide, P3 (residues 548–556) was unable to immunoprecipitate and did not neutralize HSV-1 polymerase activity, despite an anti-peptide titer comparable to the P6 and P7 antisera.

The position of two neutralization sites, consisting of nine amino acids or less was found to be within the carboxy-terminal domain of HSV-1 and HSV-2 DNA polymerase.

Production and Specificity of Antipeptide Antibodies. The sequence of the three peptides used in this study to generate antipeptide antibodies are shown in Table 1.

TABLE 1

| | Peptide Antibodies to HSV DNA Polymerase | | | |
| | | | Antibody Titer[2] | |
| Antiserum | Peptide Sequence[1] | Amino Residues | Cognate Peptide | HSV-1 Pol |
| --- | --- | --- | --- | --- |
| Control | — | — | 0 | 0 |
| P3 | LKDKKKDLSY | 548-556 | 10,000 | 0 |
| P6 | APGDEPAPPY | 1100-1108 | 12,000 | 2,000 |

TABLE 1-continued

| | Peptide Antibodies to HSV DNA Polymerase | | | |
|---|---|---|---|---|
| | | | Antibody Titer[2] | |
| Anti-serum | Peptide Sequence[1] | Amino Residues | Cognate Peptide | HSV-1 Pol |
| P7 | AGATAEETRY | 1216-1224 | 12,000 | 2,000 |

[1] Single letter amino acid code is used. L = leucine. K = lysine. D = aspartate. S = serine. Y = tyrosine. A = alanine. P = proline. G = glycine. E = glutamate. T = threonine and R = arginine The tyrosine residue (Y) has been added to facilitate coupling to BSA and thyroglobulin. Any suitable residue can be used to facilitate coupling. Any suitable amino acid can be substituted provided the antibody generated has the same function as the antibody generated against the parent peptide.
[2] Reciprocal end point dilution, as determined by ELISA.

Figure 1:
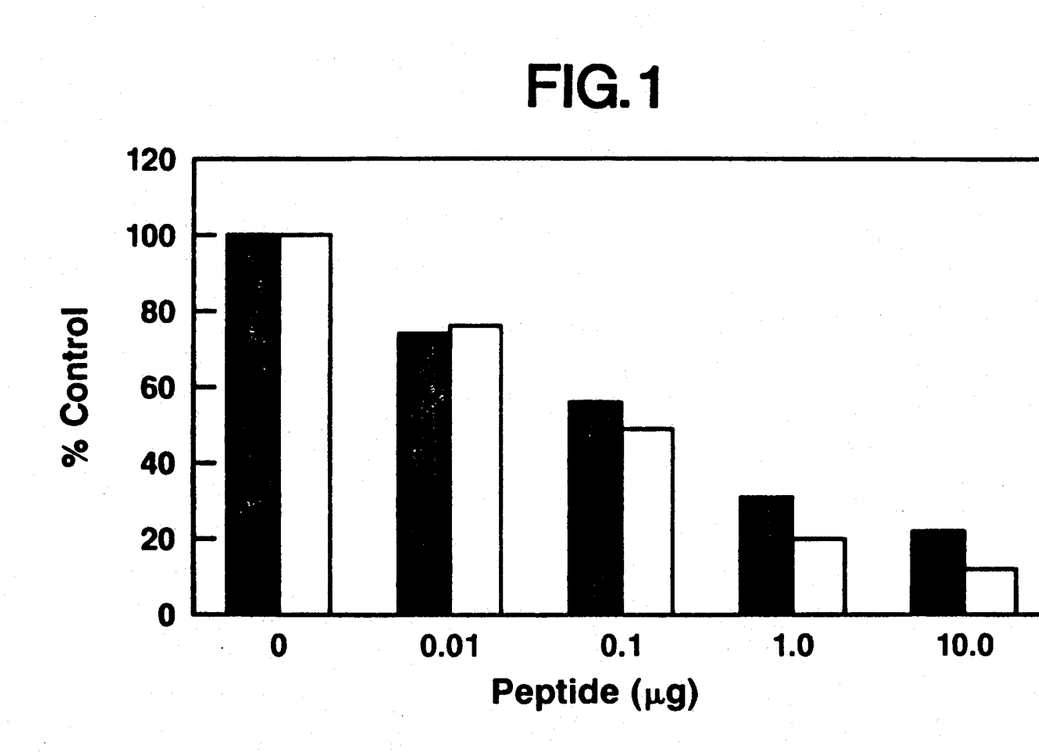
FIG. 1 shows peptide competition ELISA.

The peptides were coupled to bovine serum albumin (BSA) and thyroglobulin as described in Example 2 and were used to inoculate rabbits over a period of several months. Coupling can also be to any other suitable carrier or in an alternative embodiment of the invention the peptide need not be covalently coupled to carrier but rather can be used alone or passively absorbed to a suitable immunogen. Two rabbits were inoculated with the carrier antigen alone to produce hyperimmune control sera. The sera obtained were screened for antipeptide antibodies by ELISA using peptides (1ug) directly absorbed to the microtiter wells. The ELISA end point was arbitrarily defined as a signal three to four-fold greater than both the corresponding preimmune and hyperimmune (1:100 dilution) sera. The antibody titers generated against each peptide are shown in Table 1. These antisera were not reactive with unrelated peptides even when assayed at a 1:100 dilution. These antibodies were subsequently used in a series of ELISA assays (See Example 3) using microtiter wells coated with purified HSV (strain mP) DNA polymerase (See Example 7). The hyperimmune control and P3 sera were unreactive in this assay; both the anti-peptide P6 and P7 sera had titers of approximately 1:1000-1:2000 to this antigen (Table 1). To further demonstrate the specificity of these antisera, peptide competition ELISA assays were performed. In these experiments, purified total IgG from the hyperimmune, anti-peptide 6 and anti-peptide 7 sera were preincubated with the corresponding peptide for 30 minutes prior to addition to the polymerase coated wells. The amount of IgG selected for this assay was sufficient to produce an appreciable signal (0.250-0.300 0.D) when used alone. In FIG. 1 total rabbit IgG (approximately 2.5 ug) was incubated with 0.01, 0.1, 1.0 or 10.0 ug of the corresponding peptides for 30 minutes at room temperature in a volume of 100 ul. After 30 minutes, the reactions were added to microtiter wells which had been coated with purified HSV pol and the residual activity was determined by ELISA assay. As shown in FIG. 1, when the IgG are preincubated with their respective peptide, the ELISA signal is reduced progressively as the amount of peptide is increased. Solid boxes are results using P6 IgG and P6 peptide and Open boxes are results using P7 IgG and P7 peptide. Preincubation of anti-P6 sera with P7 or anti-P7 with P6 did not reduce the ELISA signal.

Figure 2:
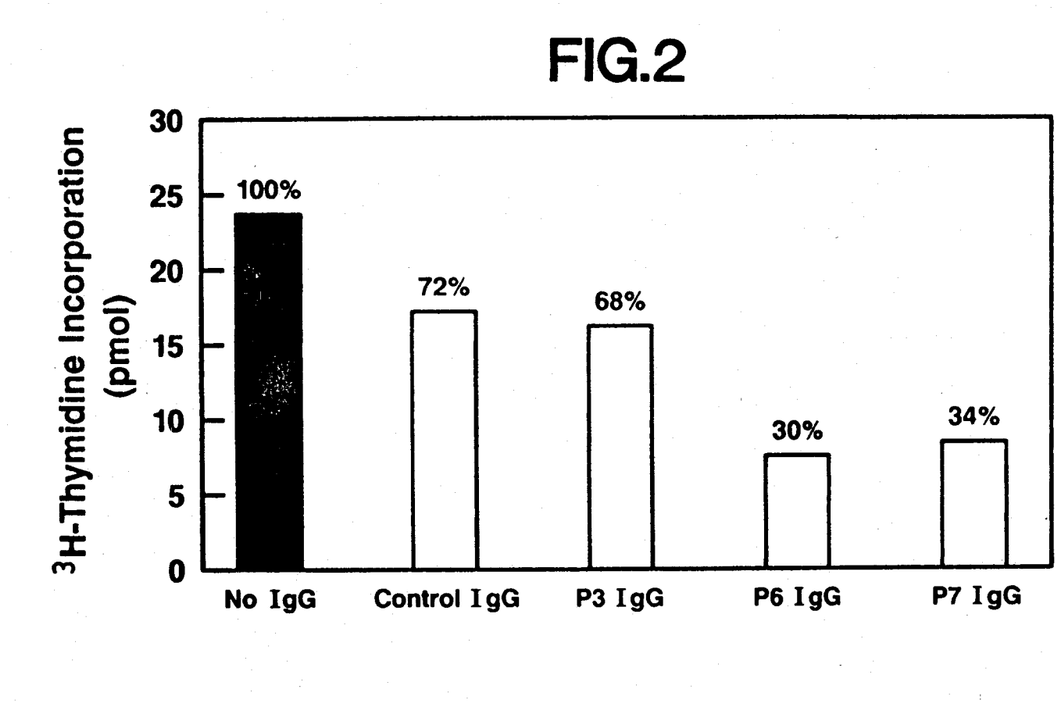
FIG. 2 shows immunopreciptiation of HSV polymerase activity.
Figure 3:
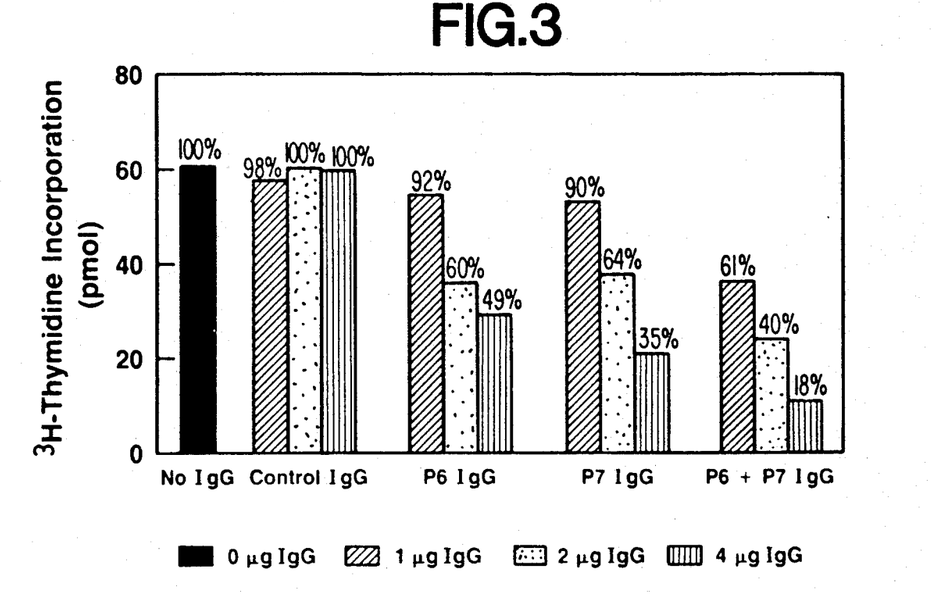
FIG. 3 shows neutralization of HSV-1 polymerase activity.

Immunoprecipitation and Neutralization of DNA Polymerase Activity. The object of these experiments was to determine whether the antibodies which specifically recognize HSV pol in the ELISA assay could affect the HSV polymerase activity in two types of assays. In the first experiments, the DNA polymerase activity was depleted from the extracts by immunoprecipitation. In FIG. 2 infected cell extracts (5ul fractions) were incubated separately with several concentrations of the appropriate antiserum for one hour. The complexes were precipitated with *Staphylococcus aureus*—Protein A (Staph A) and the residual HSV polymerase activity in the supernatants was determined. FIG. 2 shows the residual polymerase activity after the extracts had been immunoprecipitated with control hyperimmune, anti-P3, anti-P6 or anti-P7 IgG. The standard (100%) control polymerase activity was determined from extracts to which no IgG had been added. The results indicate that the addition of 2.0 ug of hyperimmune control or P3 IgG can reduce the activity approximately 25-30%, respectively. In contrast, 2ug of the anti-peptide IgG (P6 and P7) can reduce the activity 70 and 65%, respectively. These results are consistent with the polymerase ELISA and suggest specific recognition of HSV polymerase by anti-P6 and P7 IgG. However, this type of experiment is complicated by the fact that the efficiency of Staph A facilitated precipitation is variable; moreover, even with preadsorbed Staph A, non-specific reactions and adsorption to the cell wall can result in the apparent reduction of polymerase activity even when antisera to unrelated antigens are used. Such a result could be seen with hyperimmune control or P3 IgG. In order to avoid these problems and to evaluate a direct neutralization effect of these IgG's, the enzyme extracts were preincubated with the purified IgG prior to addition of the other DNA pol assay reactants. In FIG. 3 extracts from HSV-1 infected cells were preincubated with 1,2, or 4 ug of control hyperimmune, anti-P6 and anti-P7 IgG for one hour on ice. In some reactions, 0.5, 1.0 and 2.0 ug of both anti-P6 and anti-P7 IgG were added simultaneously to give total IgG concentrations of 1, 2, and 4 ug. Following incubation, the other reaction components were added and the extent of $^3$H-dTTP incorporation was determined. The neutralization of polymerase activity was then directly measured. FIG. 3 shows the results when 0, 1, 2 or 4ug of hyperimmune control, and 1, 2 or 4ug of anti-P6 or anti-P7 IgG are added to the cell extracts. Addition of up to 4 ug of the hyperimmune control IgG did not substantially or consistently reduce the extent of polymerase activity. Similar results were obtained with the P3 IgG (data not shown). In contrast, both anti-P6 and anti-P7 IgG progressively reduced the polymerase activity to approximately 49% and 35%, respectively, when 4ug was added. Moreover, when both anti-P6 and anti-P7 IgG were added at equivalent concentrations to achieve final concentrations of 1, 2, and 4 ug, the neutralization appeared additive with a final reduction of the HSV polymerase activity to approximately 80-85% of the control value.

Figure 4:
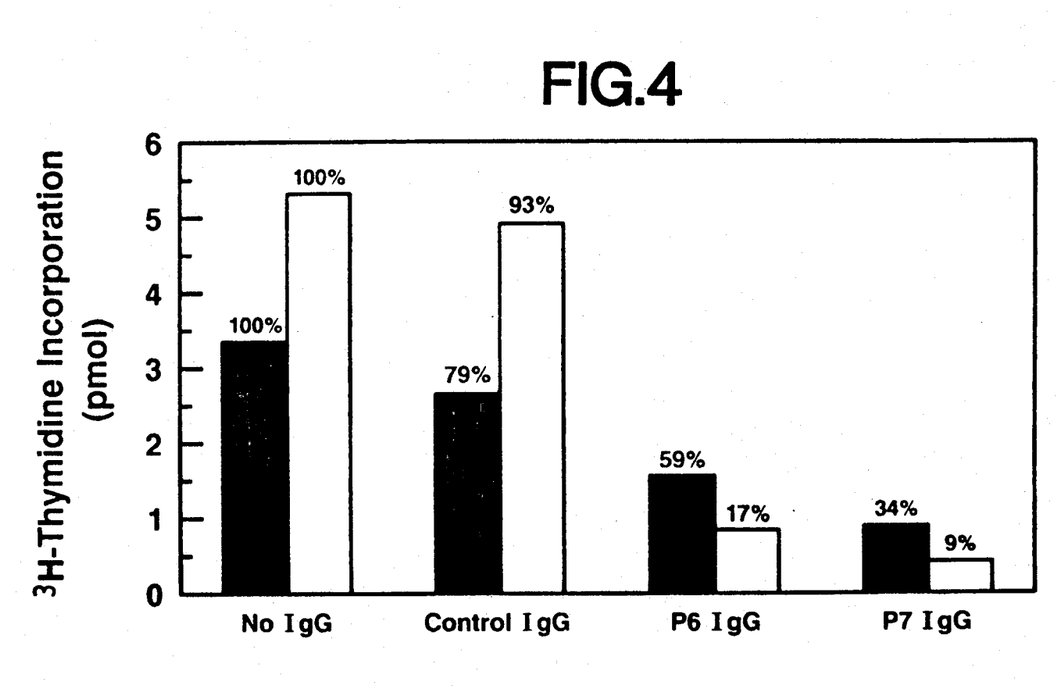
FIG. 4 shows comparative HSV neutralization.

Since the P6 and P7 sequences are conserved between HSV-1 and HSV-2, an experiment was performed to test whether the HSV-2 pol enzyme could also be neutralized with these IgG's. Cell free extracts of HSV-1 and HSV-2 infected cells were incubated with 4ug of IgG for one hour on ice. Following this incubation, the other reaction components were added and the extent of radioactivity incorporated into acid precipitable DNA was quantitated. FIG. 4 shows a comparison of HSV-1 (open box) and HSV-2 (solid box) polymerase activity following preincubation with hyperimmune control, anti-P6 and anti-P7 IgG. The difference in the total incorporation between this and previous experiments reflects the difference in cell extract protein concentrations. The results show that anti-P6 and anti-P7 IgG (4ug) can neutralize both HSV-1 and HSV-2 pol activity, although the HSV-2 activity is reduced to a lesser extent.

Figure 5:
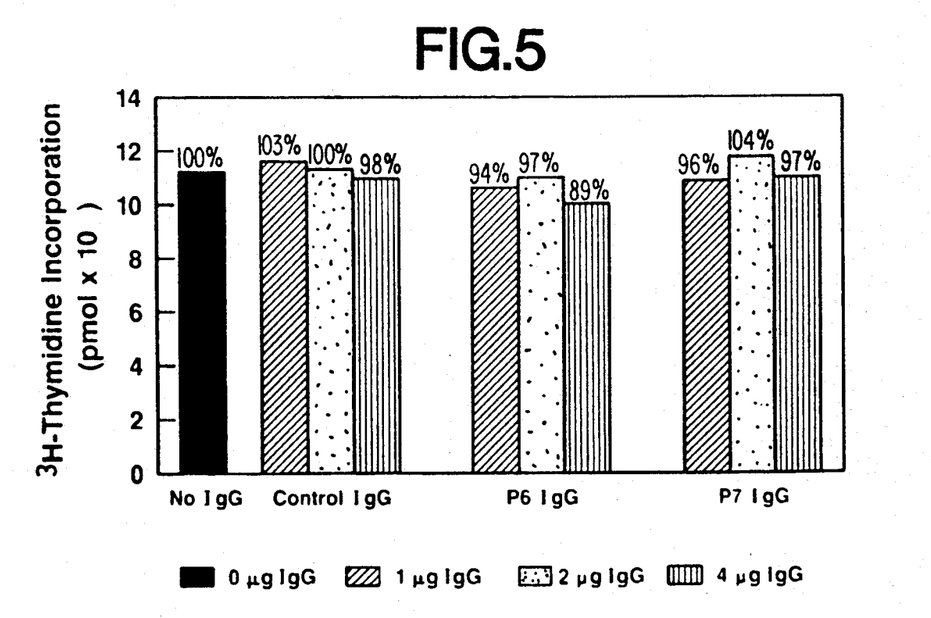
FIG. 5 shows neutralization of endogenous alpha polymerase activity.

In order to demonstrate the sequence specificity of the anti-P6 and P7 IgG's, we evaluated the ability of these reagents to neutralize the endogenous alpha polymerase activity in our extracts. Uninfected cell extracts were incubated with 1, 2 or 4 ug of control hyperimmune, anti-P6 or anti-P7 IgG for one hour on ice. Following incubation, the other reaction components were added and the extent of $^3$H-dTTP incorporation determined. FIG. 5 shows the effect of adding 0, 1, 2, or 4ug of hyperimmune control IgG or 1, 2, and 4 ug of anti-P6 or anti-P7 IgG to reactions performed under alpha polymerase the HSV-1 and HSV-2 pol activity, none of the IgG preparations significantly neutralized the alpha polymerase activity in our lysates. These results were expected, based upon the lack of the P6 and P7 sequences in the deduced alpha polymerase sequence (27).

Figure 6:
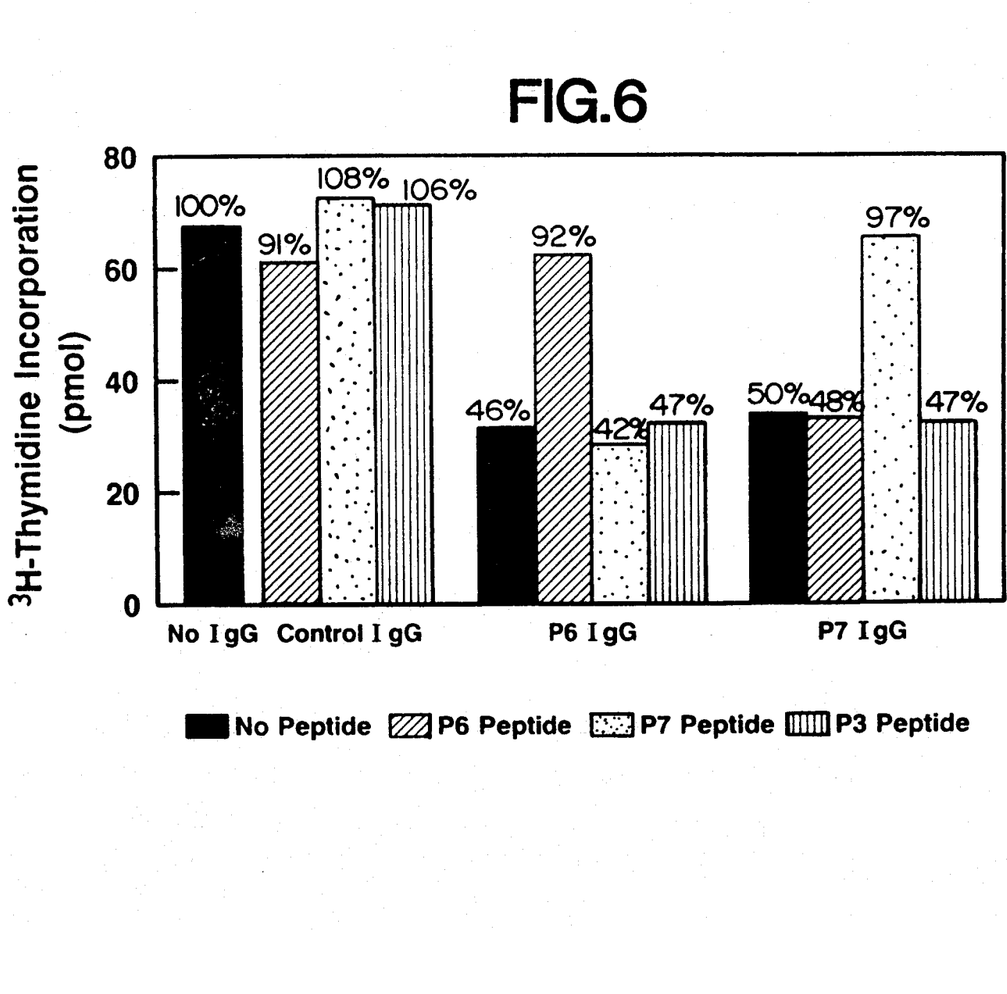
FIG. 6 shows peptide competition of HSV polymerase enzyme neutralization.

Finally, to further test the specificity of the neutralization reaction, the ability of the peptides to specifically compete with the enzyme neutralization was examined. Hyperimmune control IgG, anti-P6 and anti-P7 IgG (4ug) were preincubated without peptide or with the P3, P6 or P7 peptides (5ug) for 30 minutes on ice. Following pre-incubation, the peptide-antibody mixture was incubated with cell extracts. The other polymerase reaction components were then added and the extent of $^3$H-dTPP incorporation determined. As shown in FIG. 6, only preincubation of the anti-peptide sera with the cognate peptide resulted in the restoration of polymerase activity to near the control level. Preincubation of the extracts with the peptides alone (5ug) did not inhibit incorporation (data not shown).

Since antibodies which bind the P6 or P7 epitopes of HSV DNA polymerase can neutralize polymerase activity, P6 and P7 peptides could be used as immobilized affinity reagents to concentrate or purify compounds from natural product extracts which bind to and neutralize HSV DNA polymerase.

Alternatively, since the anti-P6 and anti-P7 antibodies recognize two determinants on HSV DNA polymerase which appear to be involved in neutralization, anti-idiotypic antibodies to the anti-P6 and anti-P7 antibodies could be useful as affinity reagents to concentrate or purify P6 or P7 binding compounds from natural product extracts.

In the preferred embodiment of the invention P6 and P7 antibodies are used to screen for compounds that bind to the P6 and P7 epitopes and subsequently prevent the binding of the cognate antibody. Since binding of antibody to either the P6 or P7 epitopes results in the neutralization of HSV DNA polymerase activity, this inhibition assay is useful to identify new antiviral agents.

In the preferred embodiment P6 and P7 peptides are separately adsorbed to microtiter plates. Each peptide (6 or 7) is a control for the specificity of the reaction with the other peptide (7 or 6, respectively).

After blocking, the plates are incubated with either buffer alone or buffered extracts of natural products or synthetic compounds.

After extensive washing, the primary antibody (hyperimmune control, anti-P6 and anti-P7) at an appropriate dilution is added to the coated wells and incubated.

After extensive washing, a conjugated secondary antibody is added to detect the amount of bound primary antibody.

The signals obtained from wells which had received buffer alone and those which have received synthetic or natural products are compared.

There are many alternative ways in which the assay could be run. In an alternative embodiment the antigen used for coating could be HSV or alpha DNA polymerase instead of the peptides. The assay would be on membranes rather than on microtiter wells. The secondary antibody could be either enzyme labelled or conjugated to a particulate indicator molecule. The buffered extract of natural products or synthetic compounds could be added after the primary antibody.

EXAMPLE 1

Viruses and cells

HSV-1 (strains Schooler or KOS) and HSV-2 (186) were propagated and titered in Vero cell monolayers. Virus was plaque purified twice prior to use.

EXAMPLE 2

Preparation of Rabbit anti-peptide sera

Peptides were coupled to a mixture of bovine serum albumin (BSA) and porcine thyroglobulin through bis-diazotized benzedine essentially as described by Bassiri (1). For the initial immunization, New Zealand White rabbits were inoculated with these conjugates at multiple subcutaneous and intradermal sites in complete Freund's adjuvant. Rabbits were bled at approximately 2 and 5 weeks post-immunization. The IgG fraction was precipitated with ammonium sulfate and purified by Protein A affinity chromatography on Perflex columns (DuPont) essentially as specified by the manufacturer.

EXAMPLE 3

ELISA Assays

For standard peptide ELISA assays, peptides (lug/100ul) were air dried onto Immulon-2 (Dynatech) wells in PBS and fixed with methanol according to Norrby et al. (16). For standard pol ELISA assays, purified pol (mP) (See Example 7) was coated onto Immulon-1 (Dynatech) wells in carbonate buffer (pH9.6) overnight at 4° C. Prior to use, both types of sensitized plates were washed with 1X ELISA WASH (Kirkegaard Perry Laboratories, KPL) and blocked at 37° C. for one hour with 1X Casein Block buffer (KPL). Following washing, the primary antibodies were added in 1X casein buffer and reacted for one hour at 37° C. The plates were washed and alkaline phosphatase conjugated affinity purified goat anti-rabbit IgG (KPL) was added for one hour. The plates were extensively washed and the p-nitrophenylphosphate substrate added for 30 minutes at room temperature. The absorbance was read immediately without quenching at 405nm (MultiScan). The ELISA end point was arbitrarily defined as a signal three to four-fold greater than both the corresponding preimmune sera (1:100) with peptide or the hyperimmune sera (1:100) in the absence of peptide.

EXAMPLE 4

DNA Polymerase Extracts

Mock infected or infected cell extracts were prepared essentially as described by Karkas et al. (11). Essentially, HeLa S3 cells were either mock infected or infected with HSV-1 (Shcooler or KOS) or HSV-2 (186) at a multiplicity of infection of 10 plaque forming unites per cell and harvested at 16 hours post infection. Cell pellets (1 × 10⁸ cells) were frozen at −80° C. Cells were thawed on ice and resuspended in 20 ml of hypotonic solution (10mM K₂PO₄, pH 7.0; 10mM Kcl; 1mM PMSF; 1mM dithiothreitol ([DTT]) and incubated on ice for 30 minutes with occasional vortexing. An equal volume of 700mM K₂PO₄; pH 7.0; 28% glycerol; 6mM DTT; 0.4% NP-40; 1mM PMSF was added and the mixture incubated on ice for an additional 30 minutes with occasional vortexing. The mixture was centrifuged for 1 hour at 125,000 x g and NP-40 added to the supernatant to a final 15 concentration of 0.4%. Aliquots were stored at −80° C. The final protein concentration of the extracts were approximately 5.0 mg/ml as determined in the Bio-Rad Bradford Assay.

EXAMPLE 5

Immunoprecipitation of DNA Polymerase Activity

Protein-A bearing *Staphylococcus aureus* (Pansorbin, Behring Diagnostics) were pretreated with BSA to minimize non-specific binding, by incubating 150 ul of cell suspension with 300 ug of BSA overnight at 4° C. The following day, the cells were pelleted, rinsed and resuspended in 125ul of 25mM Tris-HCl pH 8.0. HSV infected cell extracts (5ul) were incubated with 2 ug of purified IgG on ice for one hour. The preadsorbed Staphylococcus suspension (5ul) was added and incubation continued on ice for one hour. The mixture was centrifuged at 6500rpm (∼3000xg) in an Eppendorf microfuge and the supernatant assayed for DNA pol activity as described below. The results of assays run either without IgG or without both IgG and *Staphylococcus aureus* were averaged and used as a control value (100%).

EXAMPLE 6

DNA Polymerase Assay

The assay for alpha DNA polymerase activity was performed essentially as described previously (10,11). Reaction mixtures contained 5ul of cell extract (25ug of protein) in 10 mM Tris-Hcl; pH7.5; 10mM MgCl₂; 10 mM (NH₄)₂S₄; 0.1mM DTT; 100 um each of dATP, dCTP, dGTP; 100uM ³H-TTP (10 cpm/pmol); 40 ug/ml nicked calf thymus DNA; mM spermidine in a final volume of 50 ul. HSV DNA polymerase activity was assayed in 50 mM Tris-Cl pH 8.5, 5mM MgCl₂, 1mM DTT, 100mM (NH₄)₂SO₄, 5uM each of dATP, dCTP, dGTP, 5uM [³H]dTTP (200 cpm/pmol), 30 ug/ml DNAse I activated calf thymus DNA, and 10ug/ml BSA in a final volume of 50ul. All DNA polymerase assays were performed by incubating the reactants for 15 minutes at 37° C.; the reactions were spotted onto glass fiber filters and quenched by the addition of 10mM sodium pyrophosphate in 5% TCA. The filters were washed three times in 1N HCl, once in 95% ethanol and quantitated by scintillation counting using an LKB 1214 Rackbeta counter at 63% efficiency. All assays were conducted in duplicate. For immuno preciptiation assays, the antibody and extract were incubated on ice for 60 minutes, following the addition of Protein A *S. aureus* for an additional 60 minutes, the extracts were clarified in an Eppendorf microfuge (6500rpm, %3000xg) and the residual polymerase activity in the supernatant was assayed. For enzyme neutralization assays, the extracts were preincubated with the antibody designated in the figure legends for 60 minutes on ice prior to addition of the other components. For the competition assays, the antibodies and peptides were incubated with each other on ice for 60 minutes, prior to their addition to the reaction cocktail.

EXAMPLE 7

Reagents

Peptides were purchased from BioSearch and one major peak was apparent in the peptide portion of the profile following reversed phase (C18, Vydac) chromatography. The actual molecular weight of the synthetic peptides were demonstrated to equal the predicted molecular weight by FAB-MS (G. C. DiDonato, Department of Analytical Chemistry, Squibb Institute for Medical Research). Purified HSV DNA polymerase (strain mP) used in the pol ELISA experiments was a generous gift of W. Ruyechan (Uniformed Services University). The characteristics of this preparation have been previously described (21).

The references cited herein are as follows:

1. Bassiri, R., J. Dvorak, and R. D. Utiger. 1979. p. 46–47. In B. M. Jaffe and H. R. Behrman (ed.), Methods of hormone dioimmunoassay. Academic Press, Inc., New York.
2. Becker, Y. 1988. Computer-assisted primary and secondary structure analysis of DNA polymerases of herpes simplex, Epstein-Barr and varicella zoster viruses reveal conserved domains with some homology to DNA-binding domain in *E. coli* pol I. Virus Genes 1:351-357.
3. Challberg, M. D. 1986. A method for identifying the viral genes required for herepesivrus DNA replication. Proc. Natl. Acad. Sci USA 83:9094-9099.
4. Chartrand, P., C. S. Crumpacker, P. A. Schaffer, and N. M wilkie. 1980. Physical and genetic analysis of the herpes simplex DNA polymerase locus. Virology 103:311-326.
5. Coen, D. M., D. P. Aschman, P. T. Gelep, M. J. Retonodo, S. K. Weller, and P. A. Schaffer. 1984. Fine mapping and molecular cloning of mutations on the herpes simplex virus DNA polymerase locus. J. Virol. 49:236-247.
6. Dorsky, D. I., P. Chatis, and C. Crumpacker. 1987. Functional expression of a cloned herpes simplex type 1 DNA polymerase gene. J. Virol. 61:1704-1707.
7. Furman, P. A., M. H. St. Clarin, J. A. Fyfe, J. L. Rideout, P. N. Keller, and G. B. Elion. 1979. Inhibition of herpes simplex virus induced DNA polymerase activity and viral DNA re;ocation by 9-(2-hydroxyethoxymethyl) guanine and its triphosphate. J. Virtol 32:72-77.
8. Gibbs, J. S., H. C. Chiou, J. D. Hall, D. W. Mount, M. J. Retondo, S. K. Weller, and Dm M. Coen. 1985. Sequence and mapping analyses of the herpes simplex virus DNA polymerase gene predict a C-terminal substrate binding domain. Proc. Natl. Acad. Sci. USA 82:7969-7973.
9. Gibbs, J. S., H. C. Chiou, K. F. Bastow, Y-C Cheng, and D. M. Coen. 1988. Identification of amino acids in herpes simplex virus DNA polymerase involved in substrate and drug recognition. Proc. Natl. Acad. Sci. USA 85:6672-6676.
10. Haffey, M. L., J. T. Stevens, B. T. Terry, D. Dorsky, C. S. Crumpacker, S. M. Wietstock, W. T. Ruyechan, and A. K. Field. 1988. Expression of herpes simplex virus type 1 DNA polymerase in *Saccharomyces cerevisiae* and detection of virus-specific enzyme activity in cell-free lysates. J. Virol. 62:4493–4498.
11. Karkas, J. D., W. T. Ashton, L. F. Canning. R. Liou, J. Germershausen. R. Bostedor, B. Arison, A. K. Field and R. L. Tolman. 1986. Enzymatic phosphorylation of the antiherpetic agent 9-[2,3-dihydroxy-1-propoxy)methyl]guanine. J. Med. Chem. 29:842–848.
12. Knopf, C. W. 1986. Nucleotide sequence of the DNA polymerase gene of herpes simplex virus type 1 strain Angelotti. Nucleic Acids Res. 14:225-8226.
13. Knopf, C. W. 1987. The herpes simplex virus type 1 DNA polymerase gene: site of phosphonoacetic acid resistance mutation in strain Angelotti is highly conserved. J. Gen. Virol. 68:429-1433.
14. Kouzarides, T., A. T. Bankier, S. C. Satchwell. K. Weston, P. Tomlinson, and B. G. Barrell. 1987. Sequence and transcription analysis of the human cytomegalovirus DNA polymerase gene. J. Virol. 61:125–133.
15. Larder, B. A., S. D. Kemp and G. Darby. 1987. Related functional domains in virus DNA polymerases. EMBO J. 6:169-175.
16. Norrby, E., M. A. Mufson, H. Alexander, R. A. Houghten, and R. A. Lerner. 1987. Site-directed serology with synthetic peptides representing the large glycoprotein G of respiratory syncytial virus. Proc. Natl. Acad. Sci. USA 84:6572-6576.
17. Ostrander, M. and Y. C. Cheng. 1980. Properties of herpes simplex virus type 1 and type 2 DNA polymerases. Biochem. Biophys. Acta 609:232-245.
18. Powell, K. L. and D. J. Purifoy. 1977. Nonstructural proteins of herpes simplex virus I. Purification of the induced DNA polymerase. J. Virol. 24:618-626.
19. Purifoy, D. J. M., R. B. Lewis and K. L. Powell 1977 Identification of the herpes simplex virus DNA polymerase gene. Nature 269:621-623.
20. Quinn, J. P. and D. McGeoch. 1985. DNA sequence of the region in the genome of herpes simplex virus type 1 containing genes for DNA polymerase and the major DNA binding protein. Nucleic Acids Res. 13:8143-8163.
21. Ruyechan, W. and A. Weir. 1984. Interaction with nucleic acids and stimulation of the viral DNA polymerase by the herpes simplex virus type 1 major DNA binding protein. J. Virol. 52:727-733.
22. Thomas, M. S., L. M. Banks, D. J. Purifoy and K. L. Powell. 1988. Production of antibodies of predetermined specificity against herpes simplex virus DNA polymerase and their use in characterization of the enzyme. J. Virol. 62:1550-1557.
23. Tsurumi, T., K. Maeno and Y. Nishiyama. 1987. Nucleotide sequence of the DNA polymerase of herpes simplex type 2 and comparison with type 1 counterpart. Gene 52:129-137.
24. Tsurumi, T., K. Maeno and Y. Nishiyama. 1987. A single-base change within the DNA polymerase locus of herpes simplex type 2 can confer resistance to Aphidicolin. J. Virol. 61:2007-2015.
25. Weisshart, K. and C. W. Knopf. 1988. The herpes simplex virus type 1 DNA polymerase (Polypeptide structure and antigenic domains). Eur. J. Biochem. 174:707-716.
26. Wang, T. S., S. W. Wong and D. Korn. 1989. Human DNA polymerase a: predicted functional domains and relationships with viral DNA polymerases. FASEB J. 3:14-21.
27. Wong, S. W., A. F. Wahl, P-M. Yuan, N. Arai, B. E. Pearson, K-I. Arai, D. Korn, M. W. Hunkapiller and T. S. Wang. 1988. Human DNA polymerase alpha gene expression is cell proliferation dependent and its primary structure is similar to both prokaryotic and eukaryotic replicative DNA polymerases. EMBO J. 7:37-47.

What is claimed is:

1. A method for screening for potential inhibitors of a herpes simplex virus DNA polymerase comprising contacting the herpes simplex virus or a peptide having the amino acid sequence APGDEPAPPY or AGATAEETRY, wherein Y is any suitable amino acid residue added to facilitate coupling and function, with the potential inhibitor and an antibody made against the peptide and capable of neutralizing the herpes simplex virus DNA polymerase, and measuring the amount of antibody bound by the peptide or the herpes simplex virus DNA polymerase, wherein a decrease in antibody binding compared to a control incubation performed without the potential inhibitor is indicative of a potential inhibitor of a herpes simplex virus DNA polymerase.

2. The method according to claim 1 wherein the peptide has the amino acid sequence APGDEPAPPY, wherein Y is any suitable amino acid residue added to facilitate coupling and functioning, and the antibody is raised against this peptide.

3. The method according to claim 1, wherein the peptide has the amino acid sequence AGATAEETRY, the Y is any suitable amino acid residue added to facilitate coupling and functioning, and the antibody is raised against this peptide.

4. A method for screening for potential inhibitors of a herpes simplex virus DNA polymerase comprising:
(a) contacting the herpes simplex virus DNA polymerase or a peptide having the amino acid sequence APGDEPAPPY or AGATAEETRY, wherein Y is any suitable amino acid residue added to facilitate coupling and function, with an antibody capable of specifically binding the peptide;
(b) contacting the resulting antibody-antigen complex with the potential inhibitor; and (c) measuring the release of antibody from the antibody-antigen complex, wherein an increase in release of the antibody from the antibody-antigen complex compared to a control incubation performed without the potential inhibitor is indicative of a potential inhibitor of a herpes virus DNA polymerase.

5. The method according to claim 4, wherein the peptide has the amino acid sequence APGDEPAPPY, wherein Y is any suitable amino acid residue added to facilitate coupling and functioning, and the antibody is made against this peptide.

6. The method according to claim 4, wherein the peptide has the amino acid sequence AGATAEETRY, wherein Y is any suitable amino acid residue added to facilitate coupling and functioning, and the antibody is made against this peptide.

* * * * *